United States Patent [19]

Yamamoto et al.

[11] 3,957,442
[45] May 18, 1976

[54] APPARATUS FOR THE PRODUCTION OF GLYCEROL DICHLOROHYDRIN

[75] Inventors: Hiroaki Yamamoto; Hideo Harada; Hiroshi Miyaoka; Minoru Tanaka; Osamu Kubota; Shizuo Nakamura; Yasusi Nakamura, all of Tokyo, Japan

[73] Assignee: Asahi Denka Kogyo Kabushiki Kaisha, Tokyo, Japan

[22] Filed: Oct. 31, 1974

[21] Appl. No.: 519,614

Related U.S. Application Data

[60] Division of Ser. No. 215,564, Jan. 5, 1972, Pat. No. 3,859,367, which is a continuation-in-part of Ser. No. 867,635, Oct. 20, 1969, abandoned.

[30] Foreign Application Priority Data

Oct. 23, 1968 Japan.............................. 43-77201
Oct. 23, 1968 Japan.............................. 43-77202

[52] U.S. Cl.................................... 23/284; 23/285; 261/16
[51] Int. Cl.²........................................... B01J 1/00
[58] Field of Search.............. 23/285, 284; 260/634; 261/16

[56] References Cited

UNITED STATES PATENTS

| 2,130,226 | 9/1938 | Britton et al.......................... 260/634 |
| 2,566,355 | 9/1951 | Neuhaus.............................. 260/634 |
| 2,714,122 | 7/1955 | Smith et al........................... 260/633 |
| 3,006,739 | 10/1961 | Van Pool.............................. 23/285 |
| 3,054,831 | 9/1962 | Samples et al..................... 23/284 X |
| 3,284,169 | 11/1966 | Tominaga et al..................... 23/284 |
| 3,716,343 | 2/1973 | Chapman............................... 23/285 |
| 3,721,530 | 3/1973 | Bouchet................................ 23/285 |

Primary Examiner—Morris O. Wolk
Assistant Examiner—Arnold Turk
Attorney, Agent, or Firm—Woodhams, Blanchard and Flynn

[57] ABSTRACT

Glycerol dichlorohydrin is prepared by dissolving allyl chloride vapor in an upwardly flowing aqueous stream, dissolving chlorine gas in a separate second upwardly flowing aqueous stream to form a hypochlorous acid solution, mixing the two streams and flowing them downwardly in a reaction column where they react to form glycerol dichlorohydrin.

11 Claims, 24 Drawing Figures

APPARATUS FOR THE PRODUCTION OF GLYCEROL DICHLOROHYDRIN

CROSS REFERENCE TO RELATED APPLICATIONS

This application is a division of application Ser. No. 215,564, filed Jan. 5, 1972, now U.S. Pat. No. 3,859,367, which is a continuation-in-part of application Ser. No. 867,635, filed Oct. 20, 1969, now abandoned.

BACKGROUND OF THE INVENTION

1. Field of the Invention

This invention relates to a process and apparatus for continuously producing glycerol dichlorohydrin.

2. Description of the Prior Art

It is known that, when allyl chloride is caused to react with chlorine in the presence of water, glycerol dichlorohydrin comprising 1,3- and 1,2-isomers will be obtained in accord with the following equation:

(I)

However, generally, in this and similar chlorohydrination systems, competing secondary reactions occur producing by-products such as 1,2,3-trichloropropane and tetrachloropropyl ether according to the following equations:

These reactions interfere with the production of glycerol dichlorohydrin, reducing the yield and the quality of the product.

It is known to effect chlorohyrination of allyl chloride continuously by introducing allyl chloride in the liquid state into a vertical reaction column or tower filled with chlorine water. This method produces considerable quantities of trichloropropane, and the reaction must be carried out using an element for effecting vigorous agitation or a dispersing pump to reduce the formation of by-product. However, even in such a system the level of by-product has been undesirably high, and the yield of glycerol dichlorohydrin has been industrially unacceptably low.

There is also known a process for continuously producing glycerol dichlorohydrin by introducing gaseous allyl chloride into an environment, such as a vertical reaction column, charged with chlorine water. In this case, also, the yield of glycerol dichlorohydrin has been industrially unacceptably low.

Furthermore, when operating these prior processes so as to favor the production of a product solution of glycerol dichlorohydrin of greater than 6% w/w concentration, the yield is further reduced.

Apparatus has been suggested comprising two paired vertical columns charged with aqueous media into which are dispersed respectively chlorine gas and an olefine such as ethylene. The resulting dispersions are cross-flowed to form the charged medium of the opposite column of the pair, hence to introduce chlorine directly into the charged ethylene and to introduce ethylene into the chlorine water. As it would cause the introduction of allyl chloride directly into chlorine water, this apparatus is not satisfactory for the production of glycerol dichlorohydrin by the process involving equation (I) above.

SUMMARY OF THE INVENTION

We have discovered that the production of glycerol dichlorohydrin by the process of equation (I) above is readily feasible with a minimum of by-product formation and at solution concentrations of 4 to 6% and higher with a minimum of by-product formation. This desirable result is produced by the novel continuous cyclic process of the reaction of (1) allyl chloride solution obtained by dissolving allyl chloride vapor in a circulating aqueous medium, with (2) hypochlorous acid aqueous solution obtained by dissolving chlorine gas in a circulating aqueous medium, in which a circulating aqueous medium is continuously circulated in a reaction system due to the gas lift effect produced by the introduction of chlorine gas and allyl chloride vapor into the aqueous medium, the reaction system having at least two upward flow columns which comprise at least one chlorine dissolving column and at least one allyl chloride dissolving column, a downward flow reaction column connected at its upper and lower ends to the upper and lower ends of the upward flow columns, said process comprising the following steps:

flowing a portion of the circulating aqueous medium upwardly through said chlorine dissolving column and introducing chlorine gas into the circulating aqueous medium in the lower part of said chlorine dissolving column at a volumetric ($m^3$) rate, per unit cross-sectional area ($m^2$) of the chlorine dissolving column, per unit time (hour) in the range of from about 50 $m^3/m^2$/hour to about 300 $m^3/m^2$/hour to dissolve the introduced chlorine gas in the circulating aqueous medium to produce a hypochlorous acid solution free of chlorine gas bubbles;

flowing the remainder of the circulating aqueous medium upwardly through said allyl chloride dissolving column and introducing allyl chloride vapor into the circulating aqueous medium in the lower part of said allyl chloride dissolving column at a volumetric ($m^3$) rate, per unit cross-sectional area ($m^2$) of the allyl chloride dissolving column, per unit time (hour), in the range of from about 30 $m^3/m^2$/hour to about 300 $m^3/m^2$/hour to dissolve the introduced allyl chloride vapor in the circulating aqueous medium to produce an allyl chloride solution free of allyl chloride bubbles, the rates of introducing chlorine gas and allyl chloride vapor being regulated to maintain the molar ratio of allyl chloride/chlorine added to the aqueous medium between about 0.97 and 1.03 to 1.0;

introducing water into the circulating aqueous medium;

flowing said hypochlorous acid solution and said allyl chloride solution exiting from the upper ends of said upward flow columns into the upper end of said downward flow column and thence downwardly therein to effect mixing and reaction thereof, with the temperature being maintained in the range of from about 45°C. to about 90°C. to produce glycerol dichlorohydrin solution;

withdrawing from the reaction system a part of said glycerol dichlorohydrin solution consisting essentially of glycerol dichlorohydin, hydrochloric acid and water for recovery of glycerol dichlorohydrin therefrom; and flowing the remainder of said glycerol dichlorohydrin solution as the circulating aqueous medium to the lower ends of said chlorine dissolving column and said allyl chloride dissolving column.

This process affords the production of glycerol dichlorohydrin at a high yield and with greatly minimized production of such by-products as trichloropropane. It further affords an economically advantageous process for continuously producing glycerol dichlorohydrin at high yield and high concentration, which can be carried out in a simple form of apparatus not even requiring such circulating means as an agitator or a pump.

The circulating aqueous medium in the steps specified above in the process of this invention has the following character:

1. The circulating aqueous medium at the upper end of the chlorine dissolving column consists essentially of hypochlorous acid, glycerol dichlorohydrin, hydrochloric acid and water.

2. The circulating aqueous medium at the upper end of the allyl chloride dissolving column consists essentially of dissolved allyl chloride, glycerol dichlorohydrin, hydrochloric acid and water.

3. The circulating aqueous medium at the lower ends of the downward flow column consists essentially of glycerol dichlorohydrin, hydrochloric acid and water.

4. The circulating aqueous medium at the lower ends of the chlorine dissolving column and the allyl chloride dissolving column consists essentially of glycerol dichlorohydrin, hydrochloric acid and water.

A minor amount of unreacted allyl chloride solution may be present in the circulating aqueous medium entering the upflow columns at the position (4) above, but the amount thereof is less than 0.05% by weight of the ciuculating aqueous medium. Similarly a minor amount of unreacted hypochlorous acid solution may also be present in the medium at this time, but the amount of available chlorine is less than 0.05%, more preferably less than 0.02%, by weight of the circulating aqueous medium.

The reacting zone of the circulating system comprises the region from the upper ends of the two dissolving columns, extending downwardly into the downward flow column. By the time the circulating stream has reached the end of the downward flow column, the reaction has been substantially completed.

The above process of conducting the reaction between an allyl chloride solution and a hypochlorous acid solution features circulation of the solutions through the dissolving paths and subsequent reacting path by taking advantage of the gas lift effect produced by introducing the allyl chloride vapor and the gaseous chlorine. In order to produce glycerol dichlorohydrin continuously by reacting allyl chloride with chlorine in the presence of water, at least two upward flow columns (or long vertical towers in which the reaction mixture flows upwardly) and at least one downward flow column (or long vertical tower in which the reaction mixture flows downwardly) are connected with each other by upper connecting parts (conduits or passages) and lower connecting parts (conduits or passages) so that the reaction mixture may circulate through the reaction apparatus. The upward flow columns comprise at least one allyl chloride vapor dissolving column and at least one chlorine gas dissolving column and these columns are arranged substantially parallel with each other and are separated from each other to prevent substantially allyl chloride vapour bubbles and chlorine gas bubbles from contacting or mixing. The chlorine gas dissolving column has a means for introducing chlorine gas into the circulating aqueous mixtur at a lower par of said chlorine dissolving column to produce a hypochlorous acid solution. The allyl chloride vapour dissolving column has a means for introducing allyl chloride vapour into the circulating aqueous mixtur at a lower part of said allyl chloride dissolving column to produce an allyl chloride solution. The reaction apparatus has at least one water introducing means and at least one glycerol dichlorohydrin solution discharging means and, if necessary, a gas discharging means. Chlorine gas is introduced continuously through said means for introducing chlorine gas. Allyl chloride vapour is introduced continuously through said means for introducing allyl chloride vapour. The hypochlorous acid solution and the allyl chloride solution are mixed in the upper connecting part and are reacted in the upper connecting part or downward flow column to produce glycerol dichlorohydrin solution. Also water is introduced continuously into the reaction mixture and the produced glycerol dichlorohydrin is discharged continuously and, if necessary, excess gas is discharged.

The term "excess gas" refers to gas which is in excess of the saturation point in solubility, and therefore does not refer to unreacted allyl chloride or chlorine, since these substances are not present as gases (bubbles of gas) when the two reacting solutions are mixed. Discharge of gases such as air, carbon dioxide and nitrogen gas is effected. These gases are present in the allyl chloride and the chlorine gas feeds as impurities, and nitrogen or other nonreactive carrier gas enters the apparatus for cleaning and stripping purposes, and the residual gas is to be vented at the discharge point. Discharge means is also needed to vent excess amounts of allyl chloride or chlorine that may be introduced accidentally into the apparatus.

The vents 10 in FIGS. 1–24, which are described more fully below, are provided so that the waste gas, such as air and carbon dioxide gas, which is commonly present in allyl chloride vapour or/and chlorine gas as impurities can be vented, or gas accidentally introduced in the circulating aqueous mixture. The vent 10 in FIG. 24 is provided so that the nonreactive carrier gas, such as nitrogen gas, which is blown into the circulating aqueous mixture to strip or remove the unreacted dissolved component such as allyl chloride can be discharged. In the process of this invention, a small stoichiometric excess of allyl chloride is fed in, but it is dissolved in water to produce an allyl chloride solution free of allyl chloride vapour bubbles at the upper end of the allyl chloride dissolving column, since the allyl chloride vapour has hig solubility in water.

In the reaction apparatus to be used in the process of the present invention, the sum of the cross-sectional area(s) of the downward flow column(s) should be made equal to or larger than the sum of the cross-sectional area(s) of the allyl chloride vapour dissolving column(s) and the cross-sectional area(s) of the chlorine gas dissolving column(s).

The upward flow columns and the downward flow column(s) of the invention are generally constructed as independent columns. However, the upward flow columns and (or) the downward flow column(s) can be constructed by dividing one column or a tube inserted therein vertically with separating means, such as separating plates, into two or more parts which correspond to the upward flow column and downward flow column.

In an embodiment of the invention, the downward flow column and the upward flow columns are constructed by inserting an inner tube into an outer tube so as to form two parts composed of (1) an outside space formed between the inner wall of said outer tube and the outer wall of the inner tube and (2) the the inside space of the inner tube, and separating the outside (or inside) space by a vertical separating plate or barrier into two parts, and these three parts constitute the two upward flow columns and a downward flow column. In some embodiments of the present invention, the upward flow columns are constructed by dividing a column vertically by a barrier or separating wall into two parts which constitute an allyl chloride dissolving column and a chlorine dissolving column, or by inserting an inner tube into an outer tube so as to form two parts which comprise, respectively, an allyl chloride dissolving column and a chlorine dissolving column.

Further, in some embodiments of the present invention described above, the upper part of the barrier or the inserted inside tube wall, which separate the upward flow columns, can have small holes, slits or can be constructed of a lath as a metal lath (expanded metal) or wire lath so that the transfer of the gases or gas bubbles is prevented, but a part of the reacting solution can be transferred between them.

The cross-sections of the allyl chloride dissolving column and the chlorine dissolving column and the downward flow column can be made in any shape such as, for example, a circular or semicircular shape. However, it is preferable that they are made in a circular or semicircular shape or any shape similar to them.

Further, in feeding or introducing allyl chloride and chlorine to the reaction apparatus, it is preferable to feed them in a finely dispersed state by using, for example, nozzles or such gas dispersing plates as glass fibers.

In a preferred embodiment of the present invention, means for blowing an nonreactive gas is provided below the upper surface of the reaction mixture in the downward flow column and/or the upper connecting means to strip or remove excess raw materials from the reaction mixture, such as allyl chloride. It is most preferable to use a nitrogen gas for the nonreactive gas. The means for blowing in the nonreactive gas may be constructed, for example, by a porous tube positioned near the upper surface of the reaction mixture. It is preferable that the gas discharged from the reaction apparatus is fed to a washer, is washed with water to remove the excess allyl chloride as a solution and the obtained allyl chloride aqueous solution is cyclically reacted by feeding the solution to the lower part of the allyl chloride dissolving column.

For example, the above mentioned nonreactive gas washer can be formed by a packed tower. The discharged gas containing allyl chloride vapour and nitrogen is introduced to the lower part of the washer and is made to flow counter-currently with water. Allyl chloride is stripped as an aqueous solution, which is discharged from the bottom of the washer, and washed nitrogen is discharged from the top of the washer. It is preferable that the packings are made of porcelain and are in the form of Raschig rings.

A further preferred embodiment of the present invention comprises continuously conducting the reaction of allyl chloride with hypochlorous acid while making the reaction mixture circulate by the gas lift effect produced by introducing allyl chloride vapour and chlorine gas into an aqueous reaction mixture in the apparatus wherein, in order to continuously produce glycerol dichlorohydrin, a downward flow column is connected with at least four upward flow columns by upper connecting parts and lower connecting parts so that the reaction solution may circulate through the reaction apparatus. About half of the upward flow columns constitute allyl chloride dissolving columns and the remainder of them constitute chlorine dissolving columns. Allyl chloride vapour introducing means are provided in the lower parts of the allyl chloride dissolving columns. Chlorine gas introducing means are provided in the lower parts of the allyl chloride dissolving columns. The respective upward flow columns are connected in a substantially tangential direction to the upper part of the side wall of said downward flow column by the above mentioned upper connecting parts and, further, a water introducing means, reaction mixture discharging means and, if necessary, excess gas (or gases) withdrawing means are provided (preferably the allyl chloride dissolving columns and chlorine dissolving columns are arranged alternately and in parallel). Chlorine gas is introduced continuously through said chlorine gas introducing means into the reaction mixture to produce hypochlorous acid solution. Allyl chloride vapour is introduced continuously through said allyl chloride vapour introducing means into the reaction mixture to produce allyl chloride solution. Water is introduced continuously to the reaction mixture. The reaction mixture can flow upwardly in the upward flow columns and can flow downwardly while forming a swirling stream in the downward flow column.

Further, in the process of the present invention, it is permitted, within the scope of the present invention, to use a raw material gas of an industrial purity. Further, the raw material can be preheated and the reaction apparatus can be heated or cooled as desired. Any known conventional method can be used to separate and recover the desired component (glycerol dichlorohydrin) from the reaction product mixture.

In the process of the present invention, the reaction temperature can be a temperature at which allyl chloride will not condense, such as 45° to 90°C., preferably 55° to 90°C. For this purpose, it is preferable to provide the reaction apparatus with a jacket for adjusting the temperature.

Further, the rates of which allyl chloride and chlorine are fed to the reaction system may be such that the mol ratio of allyl chloride/chlorine can be in the range of 0.97 – 1.03/1, preferably 1.000 – 1.005/1.

Further, it is preferable that the feeding concentration of the raw material gases, that is, the ratio of the (1) total feeding amount of the allyl chloride and chlorine, per unit time, to (2) the amount of water fed in, per unit time, is in the range of 0.01 – 0.03 : 1 (1 to 30% by weight).

It is also preferable that the flow rates of the raw material gases, that is, the total volume (m³) of allyl chloride vapour and chlorine gas fed in, per unit area (m²) of the column into which they are fed, per unit time (hour), is in the range of 50 to 300 m³/m²/hour.

The reaction apparatus to be used in the process of the present invention may be of sufficient height to dissolve the fed raw material gases in water while they flow upwardly in the respective dissolving columns (or parts) and may be generally from 2 to 8 m., preferably 4 to 5 m., in height.

BRIEF DESCRIPTION OF THE DRAWINGS

Preferred embodiments of reaction apparatus to be used in the process of the present invention shall be explained with reference to FIGS. 1 to 24 in the accompanying drawings.

Figure 1:
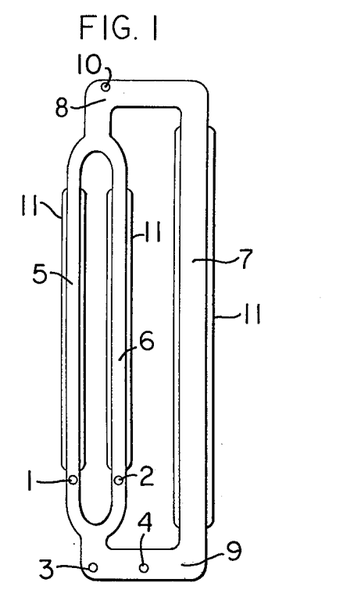
FIG. 1 is a schematic vertical section view of a reaction apparatus wherein the upward flow columns are formed by two columns arranged in parallel branches so as to comprise, respectively, an allyl chloride dissolving column and a chlorine dissolving column.

In FIG. 1, 5 is an allyl chloride dissolving column and 6 is a chlorine dissolving column. Allyl chloride vapour is fed or introduced through an allyl chloride vapour introducing means 1 at a lower part of the column 5 and chlorine gas is fed or introduced through a chlorine gas introducing means 2 at a lower part of the column 6.

Allyl chloride dissolving column 5 and chlorine dissolving column 6 and a downward flow column 7 are connected with each other by a upper connecting part or conduit 8 and a lower connecting part or conduit 9. Water is fed or introduced through a water introducing means 3 in the lower connecting part 9. The introduced allyl chloride vapour bubbles and the introduced chlorine gas bubbles rise through, respectively, the allyl chloride dissolving column 5 and the chlorine dissolving column 6 due to their buoyancy and are dissolved in the circulating aqueous mixture in the columns and chlorine is converted to hypochlorous acid. The allyl chloride solution and hypochlorous acid solution are mixed together in the upper connecting means 8, and the thus obtained reaction mixture flows downwardly through the downward flow column 7 while reacting to produce glycerol dichlorohydrin solution. The obtained glycerol dichlorohydrin solution is discharged continuously from the apparatus through a reaction product outlet port as the glycerol dichlorohydrin discharging means 4 in the lower connecting part 9. The upper connecting part 8 is provided with a vent constituted as a waste gas discharging means 10 so that the waste gas or excess gas may be vented (or discharged), if necessary. 11 is a jacket for adjusting the reaction temperature.

The same numerals 1 to 10 given in the above mentioned FIG. 1 respectively are used to identify corresponding parts in the following FIGS. 2 to 24.

Figure 2:
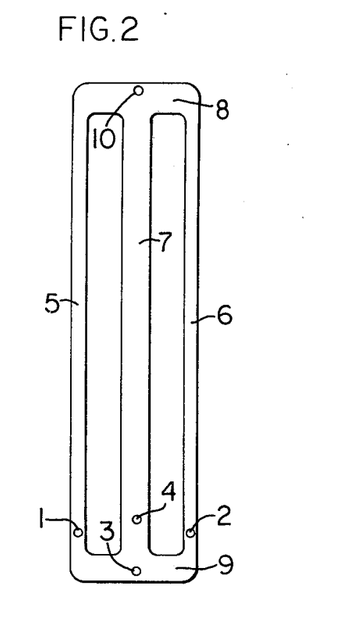
FIG. 2 is a schematic vertical section view of a reaction apparatus wherein three columns or towers are arranged in parallel and connected so that an allyl chloride dissolving column and a chlorine dissolving column are, respectively, on the left and right and a downward flow column is in the middle.

In FIG. 2, water is fed or introduced through an inlet port constituted as a water introducing means 3 in a lower connecting part 9, and the obtained glycerol dichlorohydrin solution is discharged continuously from the apparatus through a reaction product outlet port constituted as a glycerol dichlorohydrin solution discharging means 4 in the lower part of the downward flow column 7. The same operation and reaction, as are explained with reference to FIG. 1, are carried out in the case of FIG. 2.

Figure 3:
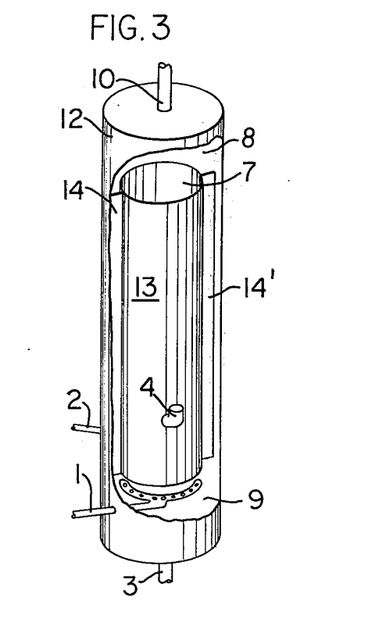
FIG. 3 is a partly cut-away perspective view of a reaction apparatus wherein the downward flow column and the upward flow columns are constructed by inserting an inside tube into an outside tube, and separating the outside space formed between the inner wall of said outside tube and the outer wall of said inside tube by vertical separating barriers into two columns forming, respectively, an allyl chloride dissolving column and a chlorine dissolving column, and the inside space of the inside tube constitutes a downward flow column.
Figure 4:
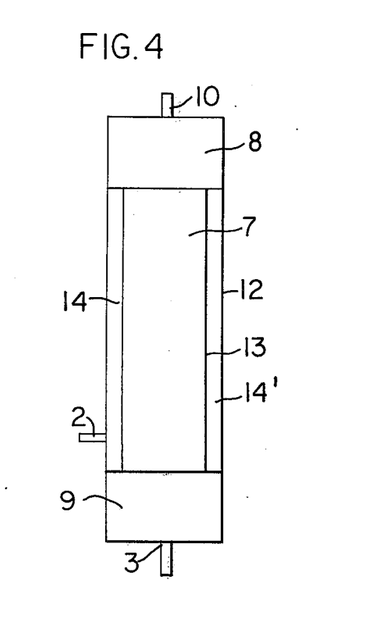
FIG. 4 is a schematic vertical section view of the reaction apparatus shown in FIG. 3.
Figure 5:
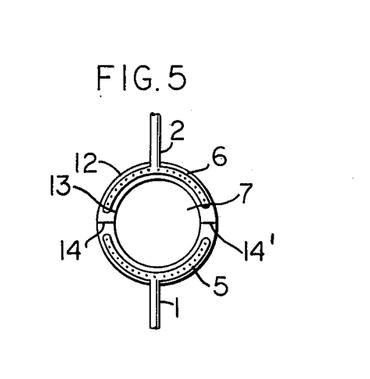
FIG. 5 is a cross-sectional view of the reaction apparatus shown in FIG. 3.

In FIGS. 3 to 5, the inside tube 13 is inserted into and positioned by fixing means in the outside tube 12, and inside tube 13 is shorter than the outside tube 12. The space between the inner wall of outside tube 12 and the outer wall of inside tube 13 is divided with two vertical separating barriers 14 and 14' into two parts to form, respectively, an allyl chloride dissolving column 5 and a chlorine dissolving column 6. The inside space of the inside tube 13 constitutes a downward flow column 7.

The space between the top wall of the outside tube 12 and the upper edge of the inside tube 13 constitutes an upper connecting part 8, and the space between the bottom wall of outside tube 12 and the lower edge of the inside tube 13 constitutes a lower connecting part 9.

Allyl chloride vapour is fed or introduced through an inlet port constituted as an allyl chloride introducing means 1 at a lower part of the allyl chloride dissolving column 5 and chlorine gas is fed or introduced through an inlet port 2 at a lower part of the chlorine dissolving column 6. Water is fed or introduced through an inlet port constituted as a water introducing means 3 in the lower connecting part 9.

The same operation and reaction as are explained above with reference to FIG. 1 are carried out in the case of FIGS. 3 to 5.

Figure 6:
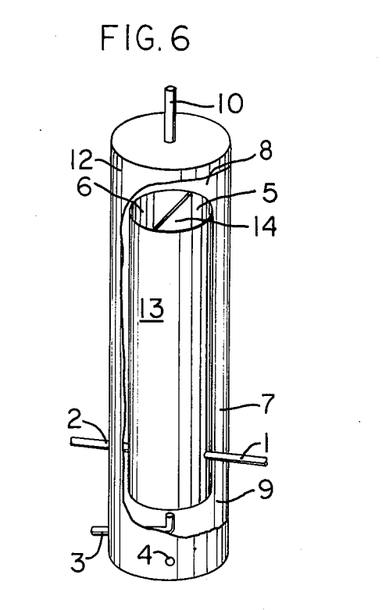
FIG. 6 is a partly cut-away perspective view of a reaction apparatus wherein the downward flow column and the upward flow columns are constructed by inserting an inside tube into an outside tube, and separating the inside space of the inside tube by a vertical separating barrier into two parts to form, respectively, an allyl chloride dissolving part and a chlorine dissolving part, and the outside space formed between the inner wall of the outside tube and the outer wall of the inside tube constitutes a downward flow column.
Figure 7:
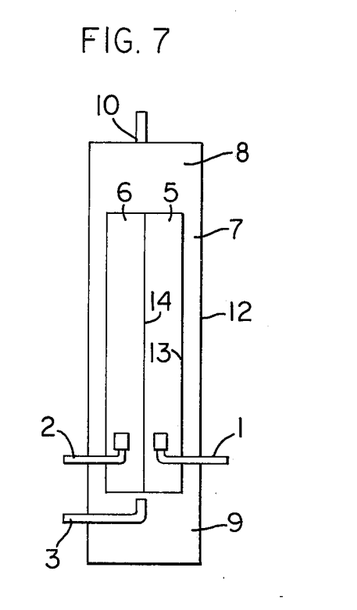
FIG. 7 is a schematic vertical section view of the reaction apparatus shown in FIG. 6.
Figure 8:
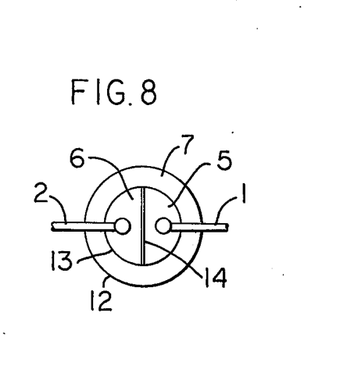
FIG. 8 is a schematic cross-sectional view of the reaction apparatus shown in FIG. 6.

In FIGS. 6 to 8, the inside tube 13 is inserted and positioned in the outside tube 12, and the inside tube 13 is shorter than the outside tube 12. The inside space of the inside tube 13 is divided with a vertical separating barrier 14 into two parts to be, respectively, an allyl chloride dissolving column 5 and a chlorine dissolving column 6. The space between the inner wall of the outside tube 12 and the outer wall of the inside tube 13 constitutes a downward flow column 7.

The space between the top wall of the outside tube 12 and the upper edge of the inside tube 13 constitutes an upper connecting part 8, and the space between the bottom wall of outside tube 12 and the lower edge of the inside tube 13 constitutes a lower connecting part 9. Allyl chloride vapour is fed or introduced through an inlet port constituting an allyl chloride introducing means 1 at a lower part of the allyl chloride dissolving column 5 and chlorine gas is fed or introduced through an inlet port constituting a chlorine introducing means 2 at a lower part of the chlorine dissolving column 6. Water is fed or introduced through an inlet port constituting a water introducing means 3 in the lower connecting part 9. And the obtained glycerol dichlorohydrin solution is discharged continuously from the apparatus through a reaction product outlet port 4 in the lower part of the lower connecting part 9. The same operation and reaction as are above explained with reference to FIG. 1 apply in the case of FIGS. 6 to 8.

Figure 9:
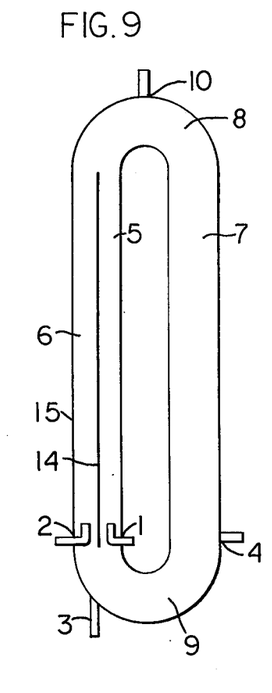
FIG. 9 is a schematic vertical section view of a reaction apparatus comprising a downward flow column and in which the upward flow columns are constructed by separating a column with a vertical separating barrier into two parts to form, respectively, an allyl chloride dissolving part and a chlorine dissolving part, which parts are connected with each other by upper and lower connecting parts.
Figure 10:
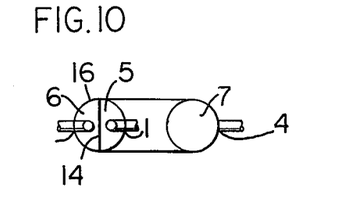
FIG. 10 is a schematic, cross-sectional view of the reaction apparatus shown in FIG. 9.

In FIGS. 9 to 10, the upward flow columns are constructed by dividing a column 15 with a vertical separating barrier 14 into two parts to form, respectively, an allyl chloride dissolving part 5 and a chlorine dissolving part 6. Allyl chloride vapour is fed or introduced through an inlet port 1 at a lower part of the allyl chloride dissolving part 5 and chlorine gas is fed or introduced through an inlet port 2 at a lower part of the chlorine dissolving part 6. Water is fed or introduced through an inlet port 3 in the lower connecting part 9. The obtained glycerol dichlorohydrin solution is discharged continuously from the apparatus through a reaction product outlet port 4 in the lower part of the downward flowing column 7. The same operation and reaction as are explained above with reference to FIG. 1 apply in the case of FIGS. 9 to 10.

Figure 11:
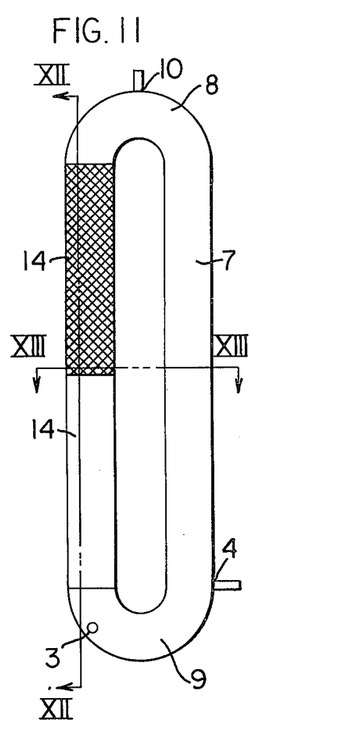
FIG. 11 is a schematic vertical section view of a reaction apparatus comprising a downward flow column and the upward flow columns are constructed by dividing a column with a vertical barrier, of which the upper half is constructed of titanium lath (of about 30 meshes), into two parts to form, respectively, an allyl chloride dissolving part and a chlorine dissolving part, which parts are connected with each other by upper and lower connecting parts.
Figure 12:
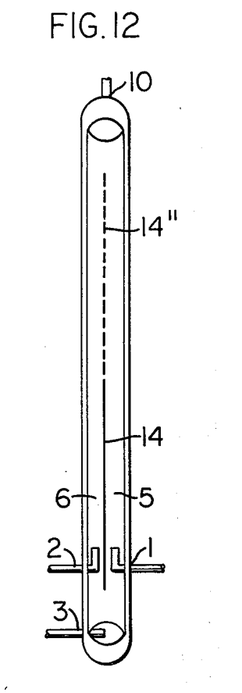
FIG. 12 is a schematic vertical sectional view taken on line XII—XII in FIG. 11.
Figure 13:
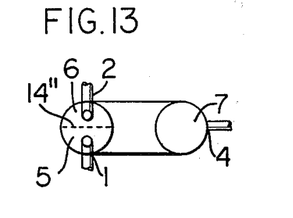
FIG. 13 is a schematic sectional view taken on line XIII—XIII in FIG. 11.

In FIGS. 11 to 13, the upward flow columns are constructed by dividing a column with vertical separating barrier 14, of which the upper half is constructed of a titanium lath 14", into two parts to form, respectively, an allyl chloride dissolving part 5 and a chlorine dissolving part 6. In the upward flow columns divided with the titanium lath 14", the transfer of the gases or gas bubbles is prevented but a part of the reacting solution can be transferred between them.

The same operation and reaction as are explained above with reference to FIG. 1 apply in the case of FIGS. 11 to 13.

Figure 14:
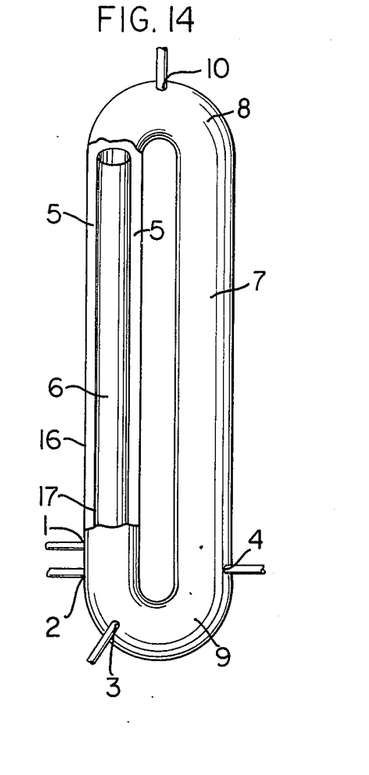
FIG. 14 is a partly cut-away perspective view of a reaction apparatus comprising a downward flow column and in which the upward flow columns are constructed by inserting an inside column into the outside column so as to divide the outside column into two parts to form, respectively, an allyl chloride dissolving part and a chlorine dissolving part, which parts are joined with the downward flow column by upper and lower connecting parts.
Figure 15:
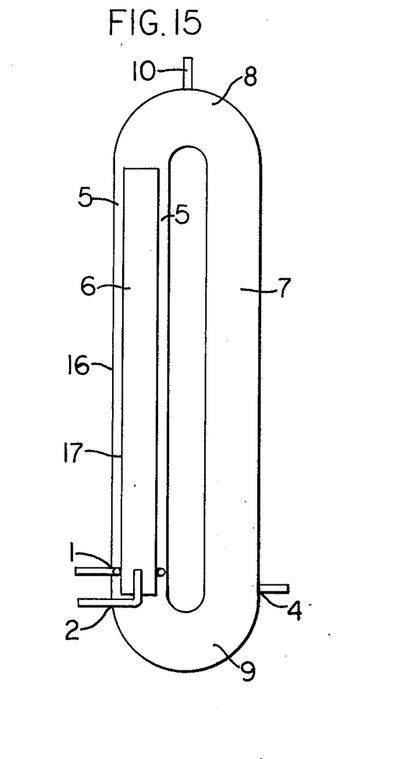
FIG. 15 is a schematic vertical section view of the reaction apparatus shown in FIG. 14.
Figure 16:
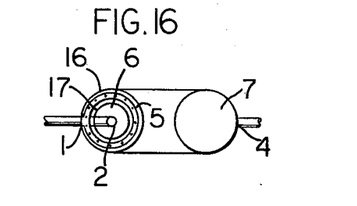
FIG. 16 is a schematic cross-sectional view of the reaction apparatus shown in FIG. 14.

In FIGS. 14 to 16, the upward flow columns are constructed by inserting an inside column 17 in the outside column 16 so as to divide the outside column 16 into two parts to be, respectively, an allyl chloride dissolving column 5 and a chlorine dissolving column 6.

Allyl chloride vapour is fed or introduced through an inlet port 1 at a lower part of the allyl chloride dissolving part 5 and chlorine gas is fed or introduced through an inlet port 2 at a lower part of the chlorine dissolving part 6. Water is fed or introduced through an inlet port 3 in the lower connecting part 9. The obtained glycerol dichlorohydrin solution is discharged continuously from the apparatus through a reaction product outlet port 4 in the lower part of the downward flow column 7. The same operation and reaction as are above explained with reference to FIG. 1 apply in the case of FIGS. 14 to 16.

Figure 17:
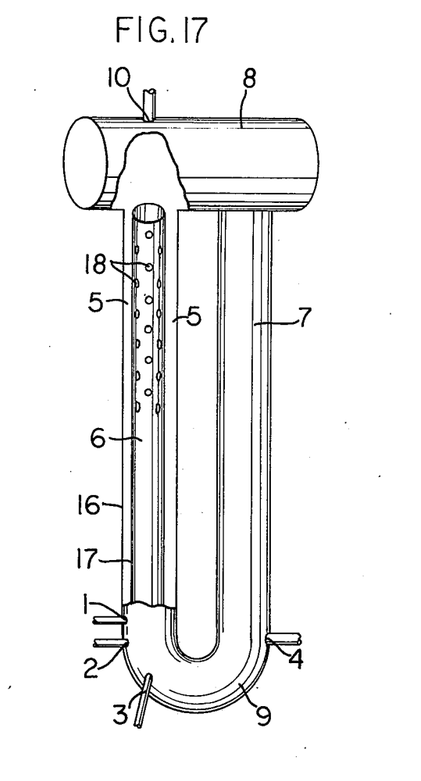
FIG. 17 is a partly cut-away perspective view of a reaction apparatus comprising a downward flow column and in which the upward flow columns are constructed by inserting an inside column into the outside column so as to divide the outside column into two parts to form, respectively, an allyl chloride dissolving part and a chlorine dissolving part, which parts ae connected (or joined) with the downward flow column by upper and lower connecting conduits, and said inside column has many small communicating holes in the upper half of it.
Figure 18:
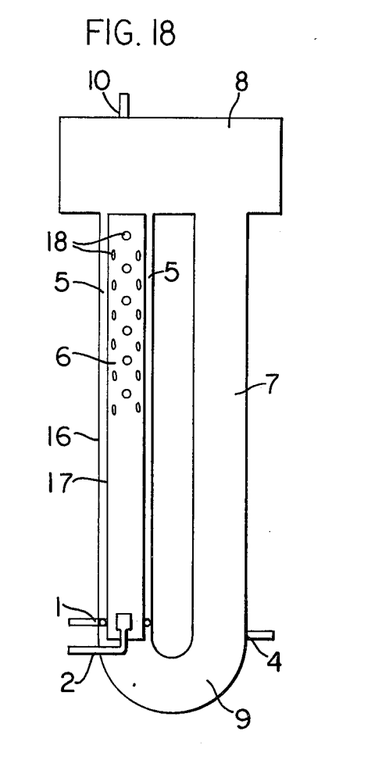
FIG. 18 is a schematic vertical section view of the reaction apparatus shown in FIG. 17.
Figure 19:
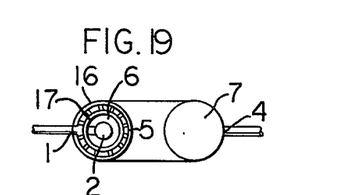
FIG. 19 is a schematic cross-sectional view of the reaction apparatus shown in FIG. 17.

In FIGS. 17 to 19, the upward flow columns are constructed by inserting an inside column 17 in the outside column 16 so as to divide the outside column 16 into two parts to be, respectively, an allyl chloride dissolving column 5 and a chlorine dissolving column 6. The inside column 17 has many small communicating holes 18 in the upper half of it.

In the upward flow columns divided with inside column 17 having many small communicating holes 18, the transfer of the gases or gas bubbles is prevented but a part of the reacting solution can be transferred between them.

The same operation and reaction as are above explained with reference to FIG. 1 apply in the case of FIGS. 17 to 19.

Figure 20:
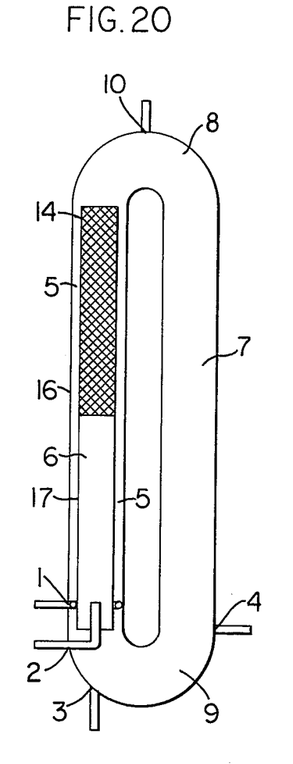
FIG. 20 is a schematic vertical section view of a reaction apparatus comprising a downward flow column and in which the upward flow columns are constructed by inserting an inside column into an outside column so as to divide the outside column into two parts to form, respectively, an allyl chloride dissolving part and a chlorine dissolving part, which parts are connected with the downward flow column by upper and lower connecting conduits, and the inside column is constructed of a titanium lath (of about 30 mesh) in the upper half of it.
Figure 21:
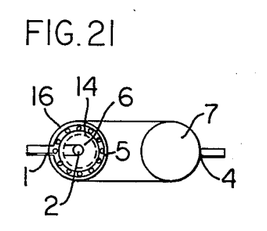
FIG. 21 is a schematic cross-sectional view of the reaction apparatus shown in FIG. 20.

In FIGS. 20 to 21, the upward flow columns are constructed by inserting an inside column 17 in the outside column 16 so as to divide the outside column 16 into two parts to be, respectively, an allyl chloride dissolving column 5 and a chlorine dissolving column 6.

The upper half of the inside column 17 is constructed of titanium lath 14.

In the upward flow columns divided with inside column 17 constructed by titanium lath 14 in the upper half of it, the transfer of the gases or gas bubbles can be prevented but a part of the reacting solution can be transferred between them. The same operation and reaction as are above explained with reference to FIG. 1 apply in the case of FIGS. 20 to 21.

Figure 22:
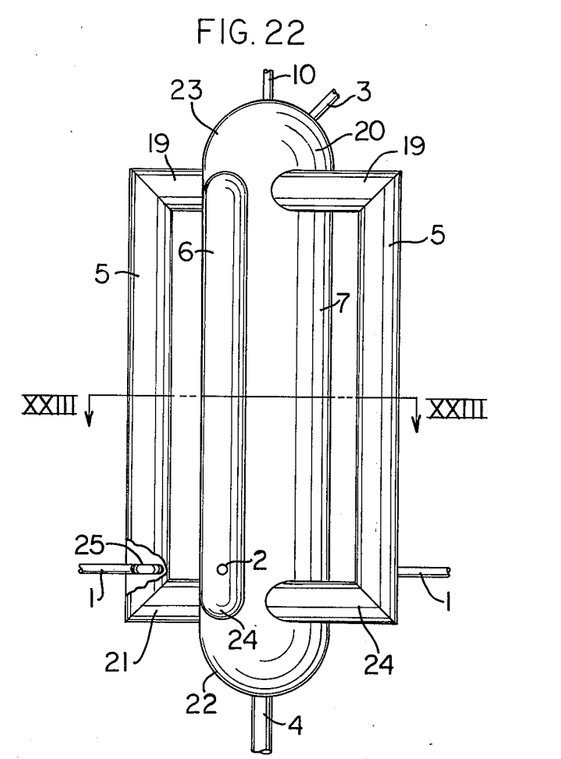
FIG. 22 is a partly cut-away elevational view of a reaction apparatus wherein the upward flow columns are comprised of four columns, two of them are allyl chloride dissolving parts and the remaining two are chlorine dissolving parts, and the four upward flow columns are connected in a tangential direction to the upper and lower parts of the side wall of a downward flow column by upper and lower connecting conduits.
Figure 23:
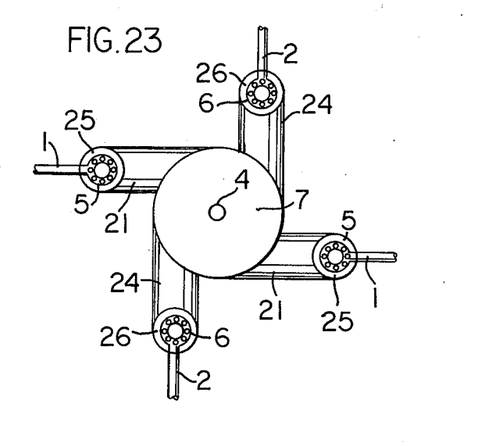
FIG. 23 is a schematic section view on line XXIII—XXIII in FIG. 22.
Figure 24:
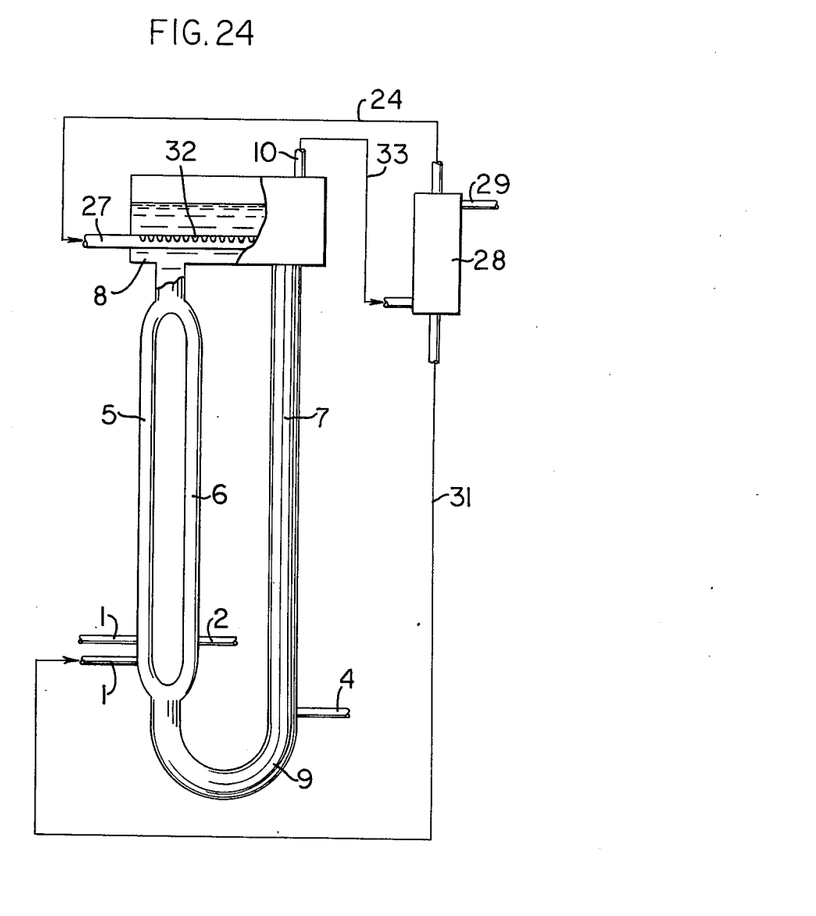
FIG. 24 is a partly cut-away view of a reaction apparatus wherein the upward flow columns are formed of two columns arranged in parallel branches so as to form, respectively, an allyl chloride dissolving column and a chlorine dissolving column, of a nonreactive gas blowing means is provided below the upper surface of the reaction mixture of the downward flow column.

In FIGS. 22 to 23, 5 is an allyl chloride dissolving column, 6 is a chlorine dissolving column and 7 is a downward flow column. Two allyl chloride dissolving columns 5 are connected in a tangential direction to the upper part 20 of the side wall of the downward flow column 7 by the upper connecting conduits 19 and are connected also in the tangential direction to the lower part 22 of the side wall of the downward flow column 7 by the lower connecting conduits 21. Also two chlorine dissolving columns 6 are connected in the tangential direction to the upper part 20 of the side wall of the downward flow column 7 by the upper connecting conduits 23 and are connected also in the tangential direction to the lower part 22 of the side wall of the downward flow column 7 by the lower connecting conduits 24. Water is fed through a water introducing means 3. Allyl chloride vapour is fed or introduced through the allyl chloride vapour introducing means 1 having the ring-shaped nozzles 25, and chlorine gas is fed or introduced through the chlorine gas introducing means 2 having the ring-shaped nozzles 26. The introduced allyl chloride vapour bubbles and the introduced chlorine gas bubbles rise through, respectively, allyl chloride dissolving columns 5 and chlorine dissolving columns 6 due to their buoyancy and are dissolved in the circulating aqueous medium in the columns and chlorine is converted to hypochlorous acid. The respective aqueous solutions are mixed together in the upper part of the downward flow column 7 and the reaction mixture flows downward while forming a swirling stream to react to produce glycerol dichlorohydrin. The obtained glycerol dichlorohydrin solution is discharged continuously from the reaction apparatus through a reaction product outlet port constituted as glycerol dichlorohydrin discharging means 4. The upper part of the downward flow column 7 is provided with a vent constituted as a waste gas discharging means 10 so that the waste gas or excess gas can be vented (or discharged), if necessary.

In FIG. 24, 5 is an allyl chloride dissolving column and 6 is a chlorine dissolving column. Allyl chloride vapour is fed or introduced through an allyl chloride vapour introducing means 1 at a lower part of the column 5 and chlorine gas is fed or introduced through a chlorine gas introducing means 2 at a lower part of the column 6.

Allyl chloride dissolving column 5 and a chlorine dissolving column 6 and a downward flow column 7 are connected with each other by an upper connecting part in the form of a tank 8 and a lower connecting part 9. A nonreactive gas blowing means 27 consisting of a porous tube having a multitude of holes 32 is provided in the lower part of the tank-shaped upper connecting part 8. Water is fed through a water introducing means 29 provided in the washer 28. The introduced allyl chloride vapour bubbles and the introduced chlorine gas bubbles rise through the allyl chloride dissolving column 5 and chlorine dissolving column 6, respectively, due to their buoyancy and are dissolved in the circulating aqueous medium in the columns and chlorine is converted to hypochlorous acid.

The allyl chloride solution and hypochlorous acid solution are mixed together in the upper connecting means 8, and the thus obtained reaction mixture flows downward through the downward flow column 7 while reacting to produce glycerol dichlorohydrin solution.

A nonreactive gas is fed through the nonreactive gas blowing means 27 provided within the tank-shaped upper connecting part 8 and is blown into the reaction mixture through the holes 32.

Thus the unreacted component (unreacted excess allyl chloride) in the reaction mixture is stripped (or degassed) and is discharged through the vent 10. The obtained mixture of the unreacted excess allyl chloride and nonreactive gas is introduced into the lower part of the washer 28 as indicated by the arrow 33.

The washer 28 is packed with Raschig rings made of porcelain. The discharged gas mixture is made to contact countercurrently with water in the washer 28.

Allyl chloride is stripped as an aqueous solution and the obtained allyl chloride solution is recycled into the allyl chloride dissolving column 5 as indicated by the arrow 31.

The washed nonreactive gas is discharged from the top of the washer 28 and is fed again to the nonreactive gas blowing means 27 as indicated by the arrow 34.

The obtained glycerol dichlorohydrin solution is discharged continuously from the apparatus through a reaction product outlet port constituted as glycerol dichlorohydrin discharging means 4.

13

In FIGS. 2 to 24, the jacket for adjusting the temperature of the reaction is omitted to simplify the drawings.

The effect of the present invention is to provide a new process wherein allyl chloride and chlorine each dissolve completely in the respective dissolving parts or columns, the reaction between the solutions takes place when they are mixed and flow downwardly so quickly that the production of such by-product as trichloropropane is minimized and glycerol dichlorohydrin is produced at a high rate of yield.

Another effect of the present invention is to provide a very economical and advantageous process for continuously producing glycerol dichlorohydrin which can be carried out with a comparatively simple apparatus without using any stirrer or pump and in which the power cost can be reduced due to the natural circulation of the system.

A further effect of the present invention is to provide a new process for continuously producing glycerol dichlorohydrin wherein a sufficiently high yield can be obtained even in the case of obtaining glycerol dichlorohydrin of a high concentration.

EXAMPLE 1

This example was carried out by using a reaction apparatus of the type shown in FIG. 1. The height of the reaction apparatus used in this example was about 5m. The distance from the allyl chloride and chlorine feeding positions 1 and 2 to the tower top was about 4m. The column diameter of each of the allyl chloride dissolving column 5 and the chlorine dissolving column 6 was 2.5 cm. (1 inch). The column diameter of the downward flow column 7 was 5 cm. (2 inches). The capacity of the apparatus was about 30 liters.

About 30 liters of a solution of 4% glycerol dichlorohydrin were charged in the above mentioned reaction apparatus and were warmed to about 60°C. with the warming jacket 11.

Then, while keeping the liquid temperature at 60°C., there were fed into the apparatus continuously an allyl chloride vapor at a feed rate of 195.0 g./hr. while being finely dispersed with a glass filter, a chlorine gas at a feed rate of 180.0 g./hr. while being also finely dispersed in the same manner and water at a feed rate of 8135 g./hr. In such case, the mol ratio of allyl chloride/chlorine was about 1.005.

Thus a solution of about 4% glycerol dichlorohydrin was continuously produced.

The yields of glycerol dichlorohydrin and the yields of the by-product in such case are shown in the following Table 1.

The yield was calculated as follows:

Glycerol dichlorhydrin yield in % based on allyl chloride $= X/Y \times 100$.

X = The glycerol dichlorohydrin produced in moles/hour.

Y = The allyl chloride feed in moles/hour.

This method of glycerol dichlorohydrin yield calculation is used in all the examples in this application.

EXAMPLES 2 and 3

A solution of each of 5.5% and 6.5% glycerol dichlorohydrin was continuously produced as in Example 1 by using the same reaction apparatus as was used in the above mentioned Example 1. The results are shown in Table 1.

Table 1

|  | Examples | | |
| --- | --- | --- | --- |
|  | 1 | 2 | 3 |
| Reaction apparatus | Figure 1 | | |
| Reaction conditions | A.C. solution - Cl$_2$ solution | | |
| A.C. feed in g./hr. | 195 | 195 | 195 |
| Cl$_2$ feed in g./hr. | 180 | 180 | 180 |
| Produced D.C.H. concentration in % | 4 | 5.5 | 6.5 |
| D.C.H. yield in % on A.C. | 98.3 | 95.0 | 90.2 |
| " " in % on Cl$_2$ | 98.0 | 93.7 | 90.3 |
| Total yield of T.C.P. and E. in % on Cl$_2$ | 0.6 | 1.8 | 2.7 |
| Concentration of A.C. in % | trace | 0.01 | 0.01 |
| Concentration of Cl$_2$ in % | trace | trace | trace |

Note : In Table 1 above, the symbols of A.C., Cl$_2$, D.C.H., T.C.P. and E. mean respectively as follows:
A.C. : Allyl chloride
Cl$_2$ : Chlorine
D.C.H. : Glycerol dichlorohydrin
T.C.P. : Trichloropropane
E. : Tetrachloropropyl ether
: Concentrations of A.C. and Cl$_2$ mean the concentration of A.C. and Cl$_2$ in the circulating aqueous mixture at the position of 9 in FIG. 1

EXAMPLE 4

This example was carried out by using a reaction apparatus of the type shown in FIG. 22. The height of the reaction apparatus used in this example was about 5 m. The distance from the allyl chloride and the chlorine feeding positions to the upper connecting part 19 of the allyl chloride dissolving column and the upper connecting part 23 was about 4 m. The column diameter of each of the allyl chloride dissolving chloride dissolving column 5 and the chlorine dissolving column 6 was 2.5 cm. (1 inch). The column diameter of the downward flow column 7 was 7.5 cm. (3 inches). The capacity of the apparatus was about 40 liters.

About 40 liters of a solution of 4% glycerol dichlorohydrin were charged in the above mentioned reaction apparatus and were warmed to about 60°C. with the warming jacket.

Then, while keeping the liquid temperature at 60°C., there were fed continuously an allyl chloride vapor at a feed rate of a total of 390 g./hr. while being finely dispersed, a chlorine gas at a feed rate of a total of 360 g./hr. while being also finely dispersed in the same manner and water at a feed rate of 16270 g./hr. In such case, the mol ratio of allyl chloride/chlorine was about 1.005.

mixture a solution of part 4% glycerol dichlorohydrin was continuously produced. mixture The yield of glycerol dichlorohydrin and the yield of the byproduct in such case are shown in the following Table 2. That is to say, glycerol dichlorohydrin was obtained at a high yield.

COMPARATIVE EXAMPLES (1) and (2)

A solution of 4% glycerol dichlorohydrin was continuously produced by making the mol ratio of allyl chloride/chlorine, respectively, of 1.06 and 0.94 as in Example 4 by using the same reaction apparatus as was used in the above mentioned Example 4.

The results are shown in Table 2.

EXAMPLES 5 and 6

A solution of each of 5.0% and 6.0% glycerol dichlorohydrin was continuously produced as in Example 4 by using the same reaction apparatus as was used in the above mentioned Example 4. The results are shown in Table 2.

Table 2

| Reaction apparatus | Examples | | | Comparative Examples | |
|---|---|---|---|---|---|
| | 4 | 5 | 6 | (1) | (2) |
| Reaction conditions | | | Figure 22 | | |
| | | A.C. solution - $Cl_2$ solution | | | |
| A.C. feed in g./hr. | 390 | 390 | 390 | 400 | 390 |
| $Cl_2$ feed in g./hr. | 360 | 360 | 360 | 350 | 385 |
| A.C./$Cl_2$ mol ratio | 1.005 | 1.005 | 1.005 | 1.06 | 0.94 |
| Produced D.C.H. concentration in % | 4.0 | 5.0 | 6.0 | 4.0 | 4.0 |
| D.C.H. yield in % on A.C. | 98.9 | 95.5 | 92.0 | 87.1 | 86.2 |
| " " in % on $Cl_2$ | 98.7 | 95.0 | 91.8 | 89.3 | 82.5 |
| Total yield of T.C.P. and E. in % on $Cl_2$ | 0.5 | 1.4 | 2.5 | 0.6 | 0.6 |
| Concentration of A.C. in % | trace | trace | 0.010 | 0.02 | trace |
| Concentration of $Cl_2$ in % | trace | trace | trace | trace | 0.02 |

Note: Concentration of A.C. and $Cl_2$ mean the concentration of A.C. and $Cl_2$ in the circulating aqueous mixture at the position of 24 in FIG. 22

EXAMPLE 7 and COMPARATIVE EXAMPLE (3)

This examples was carried out by using a reaction apparatus of the type shown in FIG. 24. The height of the reaction apparatus used in this example was about 8 m. The column diameter of each of the allyl chloride dissolving column 5 and chlorine dissolving column 6 was 2.5 cm. The column diameter of the downward flow column 7 was 5 cm.

A solution of 4% glycerol dichlorohydrin was charged in the above mentioned reaction apparatus and was warmed to about 60°C. with the warming jacket.

Then while keeping the liquid temperature at 60°C., an allyl chloride vapor and chlorine gas were fed continuously while being respectively finely dispersed with glass filters.

On the other hand, water was fed continuously through the water introducing means 29 and a nitrogen gas was fed through the nonreactive gas blowing means 27. Thus the reaction was conducted to continuously produce a solution of about 4% glycerol dichlorohydrin.

Table 3

| Examples | Example 7 | Comparative Example (3) |
|---|---|---|
| Reaction temperature in °C. | 60 | 60 |
| A.C. feed in g./hr. | 187 | 500 |
| $Cl_2$ feed in g./hr. | 170 | 438 |
| A.C./$Cl_2$ mol ratio | 1.02 | 1.06 |
| Water feed in g./hr. | 6410 | 19000 |
| $N_2$ feed in lit./hr. | 50 | 200 |
| Circulating liquid flow volume in lit./hr. | 180 | 900 |
| Produced D.C.H. concentration in % | 4 | 4 |
| D.C.H. yield in % on A.C. | 94.1 | 88.9 |
| Concentration of A.C. in % | trace | trace |
| Concentration of $Cl_2$ in % | trace | trace |

Note: Concentration of A.C. and $Cl_2$ mean the concentration of A.C. and $Cl_2$ in the circulating aqueous mixture at the position of 9 in FIG. 24.

EXAMPLES 8 and 9

A solution of 4.5% glycerol dichlorohydrin was continuously produced as in Example 1 by using the same reaction apparatus as was used in the above mentioned Example 1.

The results are shown in Table 4.

Table 4

| Examples | 8 | 9 |
|---|---|---|
| A.C. feed in g./hr. | 195 | 195 |
| $Cl_2$ feed in g./hr. | 186 | 176 |
| A.C./$Cl_2$ mol ratio | 0.97 | 1.03 |
| Produced D.C.H. concentration in % | 4 | 4 |
| D.C.H. Yield in % on A.C. | 95.4 | 96.2 |
| D.C.H. Yield in % on $Cl_2$ | 93.2 | 97.7 |
| Total yield of T.C.P. and E. in % on $Cl_2$ | 0.6 | 0.5 |
| Concentration of A.C. in % | trace | 0.01 |
| Concentration of $Cl_2$ in % | 0.01 | trace |

Note: Concentration of A.C. and $Cl_2$ mean the concentration of A.C. and $Cl_2$ in the circulating aqueous mixture at the position of 9 in FIG. 1.

In all Tables, "trace" means under 0.01%, and "Concentration of $Cl_2$" means the concentration of available chlorine in the circulating aqueous mixture.

We claim:

1. An apparatus for producing glycerol dichlorohydrin by the reaction of allyl chloride with chlorine in the presence of water, wherein an aqueous liquid reaction medium is continuously circulated in the apparatus due to the gas lift effect caused by the introduction of chlorine gas and allyl chloride vapor into the reaction medium, comprising:

at least one elongated upright chlorine-dissolving column having an inlet for chlorine gas at the lower end thereof so that a hypochlorous acid solution is formed by dissolving the chlorine gas in the reaction medium that flows upwardly through the chlorinedissolving column;

at least one elongated upright allyl chloride-dissolving column having an inlet for allyl chloride vapor at the lower end thereof so that an allyl chloride solution is formed by dissolving the allyl chloride in the reaction medium that flows upwardly through the allyl chloride-dissolving column, said allyl chloride-dissolving column and said chlorine-dissolving column being isolated from each other so that the chlorine gas in said chlorine-dissolving column does not contact the allyl chloride vapor in said allyl chloridedissolving column, and vice versa;

an upright reaction column whose upper end is connected by first passage means only to both the upper end of said chlorine-dissolving column and the upper end of said allyl chloride-dissolving column, and whose lower end is connected by second passage means only to both the lower end of said chlorine-dissolving column and the lower end of said allyl chloride-dissolving column, whereby the reaction medium containing the hypochlorous acid solution leaving the upper end of said chlorine-dissolving column and the reaction medium containing the allyl chloride solution leaving the upper end of said allyl chloride-dissolving column mix and flow through said first passage means and thence downwardly through said reaction column and react to produce a reaction medium mixture containing glycerol dichlorohydrin solution and said reaction medium mixture then flows through said second passage means to the lower ends of said chlorine-dissolving column and said allyl-chloride dissolving column and then upwardly therein as the reaction mediums;

outlet means for continuously withdrawing a portion of the reaction medium mixture containing glycerol dichlorohydrin solution from the apparatus;

and water inlet means for introducing water into the apparatus to make up for the reaction medium mixture containing glycerol dichlorohydrin solution withdrawn from the apparatus.

2. An apparatus as claimed in claim 1 wherein said first passage means and said second passage means extend tangentially to the wall of said reaction column.

3. An apparatus as claimed in claim 1 including means for blowing a non-reactive gas into the reaction medium mixture in the upper part of the apparatus, and means for discharging from the apparatus said non-reactive gas and unreacted gas present in said reaction medium mixture.

4. An apparatus as claimed in claim 3 wherein said first passage means and said second passage means extend tangentially to the wall of said reaction column.

5. An apparatus as claimed in claim 1, wherein said outlet means is located close to the bottom of said reaction column and said water inlet means is located downstream of said outlet means and close to the bottoms of said chlorine-dissolving column and said allyl chloride-dissolving column.

6. An apparatus as claimed in claim 5 in which all said columns are defined by an upright outer tube, an upright inner tube disposed within said outer tube and spaced therefrom, two upright barrier walls extending between said inner and outer tubes and dividing the space therebetween into two sections, one of which defines the chlorine-dissolving column and the other of which defines the allyl chloride-dissolving column, said inner tube defining said reaction column, the upper and lower ends of said inner tube being spaced inwardly from the corresponding ends of said outer tube to define said first and second passage means between said upper ends and said lower ends, respectively.

7. An apparatus as claimed in claim 5 in which all said columns are defined by an upright outer tube, an upright inner tube disposed within said outer tube and spaced therefrom, an upright barrier wall extending across said inner tube and dividing same into two sections, one of which defines the chlorine-dissolving column and the other of which defines the allyl chloride-dissolving column, said outer tube defining said reaction column, the upper and lower ends of said inner tube being spaced inwardly from the corresponding ends of said outer tube to define said first and second passage means between said upper ends and said lower ends, respectively.

8. An apparatus as claimed in claim 5 in which said chlorine-dissolving column and said allyl-chloride dissolving column are defined by a single conduit having an internal barrier wall dividing same into two sections, one of said conduit sections defining the chlorine-dissolving column and the other of said conduit sections defining the allyl chloride-dissolving column.

9. An apparatus as claimed in claim 8 wherein said barrier wall has a perforate upper section to permit the reaction mediums to transfer between said columns, but to prevent gas from transferring between said columns.

10. An apparatus as claimed in claim 5 in which said chlorine-dissolving column and said allyl-chloride dissolving column are defined by an outer conduit and an inner conduit disposed within and spaced from said outer conduit, said inner conduit defining one of said columns and the space between said conduits defining the other of said columns.

11. An apparatus as claimed in claim 10 wherein said inner conduit has a perforate upper section to permit the reaction mediums to transfer between said columns, but to prevent gas from transferring between said columns.

* * * * *